US012791073B2

(12) United States Patent
Herr et al.

(10) Patent No.: US 12,791,073 B2
(45) Date of Patent: Nov. 10, 2026

(54) LEAF SPRING WITH HIGH RESOLUTION STIFFNESS CONTROL

(71) Applicant: Massachusetts Institute of Technology, Cambridge, MA (US)

(72) Inventors: Hugh M. Herr, Concord, NH (US); Emily Ann Rogers-Bradley, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 726 days.

(21) Appl. No.: 18/044,346

(22) PCT Filed: Sep. 8, 2021

(86) PCT No.: PCT/US2021/049526
§ 371 (c)(1),
(2) Date: Mar. 7, 2023

(87) PCT Pub. No.: WO2022/056037
PCT Pub. Date: Mar. 17, 2022

(65) Prior Publication Data
US 2023/0366442 A1 Nov. 16, 2023

Related U.S. Application Data

(60) Provisional application No. 63/075,901, filed on Sep. 9, 2020.

(51) Int. Cl.
*F16F 1/22* (2006.01)
*A61F 2/66* (2006.01)
(Continued)

(52) U.S. Cl.
CPC .................. *F16F 1/22* (2013.01); *A61F 2/66* (2013.01); *A61F 2002/503* (2013.01);
(Continued)

(58) Field of Classification Search
CPC .... F16F 1/22; F16F 2228/066; F16F 2230/18; F16F 2230/40; F16F 2238/022;
(Continued)

(56) References Cited

U.S. PATENT DOCUMENTS 1,922,001 A * 8/1933 Goltry ........................ F16F 1/18 267/47
6,663,673 B2 12/2003 Christensen
(Continued)

FOREIGN PATENT DOCUMENTS

DE 102011053765 A1 3/2013

OTHER PUBLICATIONS

International Search Report and Written Opinion for Int'l Application No. PCT/US2021/049526, Date of Mailing: Feb. 8, 2022.

*Primary Examiner* — Bruce E Snow
(74) *Attorney, Agent, or Firm* — Hamilton, Brook, Smith & Reynolds, P.C.

(57) ABSTRACT

A variable stiffness leaf spring mechanism and method of locking parallel leaf springs allow for a wide range of stiffness settings in a low-mass package. By varying the number of parallel leaf springs as well as the thickness and stiffness of each layer the system stiffness and range of stiffness settings can be optimally tuned to each application. Additionally, by locking leaf springs without inducing large normal forces from a clamping mechanism, the frictional wear on the system is greatly diminished. In addition to increasing the life cycles of the system, this will decrease auditory noise emitted during operation. The system and method can be applied to lower extremity prostheses to allow for more biological emulation than passive prostheses in a lower mass package than powered prostheses.

19 Claims, 15 Drawing Sheets

(51) Int. Cl.
*A61F 2/50* (2006.01)
*A61F 2/68* (2006.01)
*A61F 2/70* (2006.01)

(52) U.S. Cl.
CPC ................ *A61F 2002/6664* (2013.01); *A61F 2002/6845* (2013.01); *A61F 2002/701* (2013.01); *F16F 2228/066* (2013.01); *F16F 2230/18* (2013.01); *F16F 2230/40* (2013.01); *F16F 2238/022* (2013.01)

(58) Field of Classification Search
CPC ..... F16F 1/182; F16F 1/26; A61F 2/66; A61F 2002/503; A61F 2002/6664; A61F 2002/6845; A61F 2002/701; A61F 2002/5056; A61F 2002/5079; A61F 2002/607; A61F 2002/6614; A61F 2002/7615; A61F 2002/7887; A61F 2/60; A61F 2/78; B60G 2206/428; B60G 2500/22
USPC ............................................ 267/47, 48, 265
See application file for complete search history.

(56) References Cited

U.S. PATENT DOCUMENTS

| | | | | |
|---|---|---|---|---|
| 6,767,370 | B1 | 7/2004 | Mosler et al. | |
| 7,172,630 | B2 | 2/2007 | Christensen | |
| 7,527,253 | B2 | 5/2009 | Sugar et al. | |
| 2004/0064195 | A1 | 4/2004 | Herr | |
| 2006/0255556 | A1* | 11/2006 | Reast ..................... | B60G 11/12 280/124.17 |
| 2015/0289996 | A1 | 10/2015 | Smith | |
| 2015/0305894 | A1 | 10/2015 | Mosler | |
| 2016/0081821 | A1 | 3/2016 | Sandahl | |
| 2023/0366442 | A1* | 11/2023 | Herr .......................... | A61F 2/66 |

* cited by examiner

LEAF SPRING WITH HIGH RESOLUTION STIFFNESS CONTROL

RELATED APPLICATION

This application is the U.S. National Stage of International Application No. PCT/US2021/049526, filed on Sep. 8, 2021, which designates the U.S., published in English, and claims the benefit of U.S. Provisional Application No. 63/075,901, filed on Sep. 9, 2020. The entire teachings of the above applications are incorporated herein by reference.

GOVERNMENT SUPPORT

This invention was made with Government support under W911NF-17-2-0043 awarded by the U.S. Army Research Office. The Government has certain rights in the invention.

BACKGROUND OF THE INVENTION

There are several existing patents and research devices for tunable quasi-passive variable stiffness prostheses. A similar invention by Herr proposes the use of parallel leaf springs to modify spring stiffness of the device [1]. However, this invention only allows for adjacent leaf springs to be locked together, greatly decreasing the number of possible stiffness settings. By instead allowing for each individual layer to be locked or unlocked independently, the number of possible stiffness settings is greatly increased. Other inventions exist that use clamping mechanisms to prevent relative sliding between layers [1]. The drawback of these mechanisms is that they rely on increasing the normal force between layers, increasing friction and causing high rates of sliding contact friction and wear between layers.

Another patent exists that utilizes a variable viscosity fluid between two parallel leaf springs to increase stiffness of the device [2]. This mechanism uses similar mechanical properties to the proposed invention, but uses only 2 parallel leaves instead of multiple.

Glanzer et al. present a variable stiffness foot prosthesis that adjusts the fulcrum point of a beam in bending to vary stiffness [3]. This device uses a belt drive to change the position of a sliding fulcrum, allowing for the adjustment of forefoot beam length, similar to the VSPA foot designed by Shepherd. This device has the same limitations as [4], with increased distal mass.

Another variable stiffness prosthesis allows for continuous adjustment of stiffness by changing the effective length of a cantilever beam [4] [5]. This device uses a lead screw driven linear actuator to change the position of the fixed end of the beam, changing the length of the beam and changing the bending stiffness [5]. The device presented by Shepard et al. [5] relies on an additional beam which adds mass and complexity to the system, and has a lead screw actuator along the length of the foot, which makes the forefoot stiffness of the device overly stiff.

SUMMARY

A variable stiffness spring assembly comprises multiple leaf springs joined to bend together and to slide relative to each other, with ends of the leaf springs displaced axially relative to each other with bending and a mechanical ground. Each of multiple actuators is associated with an individual leaf spring of the multiple leaf springs, each actuator limiting axial displacement of an end of the individual leaf spring relative to the mechanical ground independent of other leaf springs. A controller is configured to control each actuator.

Each actuator may limit axial displacement of the individual end of the spring by locking the end of the individual spring to the mechanical ground. Each actuator may lock the end of the individual spring to the mechanical ground by extending a pin through the individual spring and the mechanical ground. The pin may extend through slots in leaf springs other than the individual spring.

Each actuator may lock the end of the individual spring to the mechanical ground through an electrostatic clutch.

Each actuator may limit axial displacement of an end of the individual spring by applying tension to a cable coupled between the end of the individual spring and the mechanical ground. The cable may be controlled through a worm gear.

Each actuator may limit axial displacement of the end of the individual spring through a variable damper coupled between the end of the individual spring and the mechanical ground.

Each actuator may limit axial displacement of the end of the individual spring through a lead screw coupled between the end of a leaf spring and the mechanical ground. The actuator may be a motor that rotates the lead screw. The actuator may be a variable damper coupled to the lead screw. The actuator may be a clutch coupled to the lead screw.

The mechanical ground may comprise a leaf spring.

The variable stiffness spring assembly may be configured as or otherwise be applied to a lower extremity prosthesis.

A variable spring assembly may comprise multiple leaf springs joined to bend together and to slide relative to each other with ends of the leaf springs displaced axially relative to each other with bending; and electrostatic clutches may extend between adjacent leaf springs to join the adjacent leaf springs.

A method of varying spring stiffness comprises providing multiple leaf springs joined to bend together and to slide relative to each other, with ends of the leaf springs displaced axially relative to each other with bending, and a mechanical ground. Axial displacement of an end of each leaf spring is limited relative to the mechanical ground independent of other leaf springs.

In the method, axial displacement may be limited by multiple actuators, each actuator associated with an individual leaf spring of the multiple leaf springs, and a controller configured to control each actuator.

DETAILED DESCRIPTION OF THE INVENTION

Figure 1:
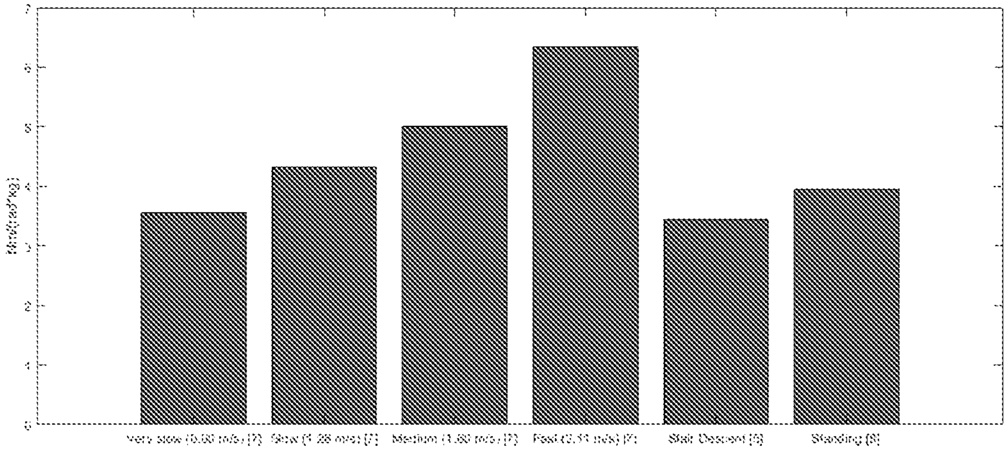
FIG. 1: Stiffness of a biological ankle during walking, standing, and stair descent.

A method is provided for automatically adjusting the bending stiffness and damping properties of a cantilever beam spring. Bending stiffness of leaf springs is tuned by changing the moment of inertia of the springs. By automatically locking and unlocking parallel springs, a large number of different stiffness states can be achieved.

There are 3 fundamental ways of changing bending stiffness of a cantilever beam:

a) The length of the beam can be adjusted to change the bending stiffness of a cantilever beam. The approximate bending stiffness of a cantilever beam is given by:

$$k = \frac{3EI}{l^3},$$

where E is the Young's modulus of the material, I is the area moment of inertia of the beam, and 1 is the beam length. Increasing 1 leads to a decrease in stiffness, decreasing 1 increases stiffness.

b) A second way of adjusting stiffness is to add additional spring in parallel. Similar to how stiffness is controlled in biological joints, adding additional springs in parallel leads to a stiffer joint. For the bending stiffness of a beam, if we add parallel beams that are also bending, our stiffness will increase.

c) A third method is the moment of inertia of a beam in bending can be increased, increasing the bending stiffness.

The area moment of inertia, I, for a rectangular beam at its centroid is governed by the equation $$I = \frac{bh^3}{12},$$

where b is the beam width and h is the beam height. Changing moment of inertia of the beam changes bending stiffness. As mentioned above, the stiffness of a cantilever beam is given by:

$$k = \frac{3EI}{l^3}.$$

Increasing I (moment of inertia) will increase the bending stiffness, decreasing I decreases bending stiffness. Due to the cubed h term in the area moment of inertia, by joining two parallel beams together, the effective thickness increases and the stiffness is greater than 2 beams in parallel. The stiffness of n parallel beams of equal bending stiffness is $k_{total}=n*k_{individual}$, whereas the stiffness for a beam of increased thickness equal to n beams of b thickness is $k_{total}=n^3*k_{individual}$. Parallel springs are locked to a mechanical ground; a body at the output of the load path, which connects the parallel leaf springs to the load applied to the system. This effectively increases the thickness of the beam, and stiffness approaches the stiffness governed by the equation for a spring of increased h. Additionally, locking non-adjacent springs to a mechanical ground increases the number of possible stiffness settings. The parallel axis theorem explains that the moment of inertia increases as the bending axis is moved farther from the centroid: $I_{parallel}=I_c+Ad^2$, where $I_c$ is the centroidal moment of inertia, A is the cross-sectional area, and d is the distance between the centroidal axis and the bending axis. As a beam is locked to the mechanical ground, for springs farther from the bending axis the moment of inertia and therefore the bending stiffness is increased, such that locking spring 1 to ground is stiffer than locking spring 4 to ground. Therefore the proposed invention with n leaf springs has independent stiffness settings equal to C(n, 1)+C(n, 2)+ . . . +C(n, n), where C(n, m) refers to the mathematical combination of n and m—the distinct number of sets of m springs that can be formed from the total of n springs. For example, for a mechanism with 4 independently controlled leaf springs, the total stiffness settings are C(4,1)+C(4,2)+C(4,3)+C(4,4)=4+6+4+1=15.

Disclosed embodiments allow the mechanical properties of a leaf spring to be controlled in the following ways:

a) Pure stiffness control to tune the force-displacement curve to a desired constant value.

b) Damping control to tune viscoelastic properties of bending.

c) Control the linearity or non-linearity of stiffness or dampening by actuating the mechanisms at specific times throughout bending.

d) Energy storage by locking leaf spring in a bent configuration.

e) A combination of damping and stiffness control, either linear or non-linear.

The embodiments improve upon the prior art by using the structure of the prosthesis as the spring mechanism rather than relying on a secondary beam, which decreases overall mass of the system. The embodiments allow for n layers to be independently tuned, where the number of stiffness settings of the device is equal to C(n, 1)+C(n, 2)+ . . . +C(n, n). In addition, the mechanism used to prevent leaf spring sliding uses a locking mechanism rather than increasing normal forces at the spring interface, which decreases frictional forces between the layers and therefore decreases rate of wear and noise of operation. A bearing surface is adhered between each spring layer to decrease sliding friction and decrease wear rates. The leaf spring may be made of carbon fiber composites, fiber glass, steel, or any other material with a high stiffness. The bearing surface may be made of UHMW, PTFE, Teflon, or another similar bearing surface.

This invention describes a novel method for mechanically adjusting the stiffness of leaf springs in a low-power quasi-passive device. The proposed invention locks layers of a multi-layer leaf spring system, preventing layers from sliding relative to each other, thus increasing the stiffness of the device.

Potential Markets

This invention has potential commercial applications for lower-extremity prostheses. Prosthetic companies will be interested in this technology due to the ability to automatically tune a prosthesis to match biological stiffness levels in a low mass and low power package. This technology also has potential applications for exoskeleton devices. Exoskeleton or orthosis companies may be interested in lightweight, variable stiffness mechanisms for assistive or augmentative devices.

The present invention includes two major classes of embodiments. The first major class provides for actively controlled passive stiffness parameters. This class of embodiments will be referred to as variable-stiffness embodiments. Variable-stiffness embodiments include:

a) Pin locking system for stiffness adjustment
b) Cable driven worm gear locking system
c) Small non-backdrivable linear actuator locking system
d) Electro-static clutching locking system The second major class of embodiment is variable-dampening systems. This embodiment of the present invention allows for actively controlling damping properties of the system through viscoelastic materials. Variable-dampening embodiments include:

e Adjustable hydraulic dampers to control viscoelasticity.

The variable stiffness and variable dampening classes can be used independently or in conjunction to tune both stiffness and dampening properties of leaf springs. The variable stiffness embodiments can prevent relative sliding between the leaf springs by locking the springs in discrete positions, such as in embodiment a, or locking can be done continuously, such as in embodiments b, c, and d. Continuous locking positions allow for tuning the effect of the stiffness adjustment. Stiffness can be tuned to be linear or non-linear depending on the desired mechanical behavior. Hardening or softening springs can be created by locking or unlocking individual leaf springs at different positions throughout bending. In addition, energy can be stored in a spring by mechanically bending the spring, locking the sliding to hold the spring in the bent configuration, and then releasing the stored energy when desired. Additionally, the dampers can be used to dissipate mechanical energy as heat in a controlled manner to create the ideal mechanical properties.

Embodiments make possible prostheses that have tunable mechanical properties as a function of joint position, angular velocity, torque, and gait phase. Prostheses can mechanically adjust stiffness and damping properties as a function of patient size, walking speed, terrain, ground compliance, and phase of gait cycle. Prostheses will be better able to mimic the mechanical properties of biological limbs. Such a prosthesis may include a running specific prosthesis as well as a walking prosthesis.

Prostheses may have multiple sections of tunable leaf springs. As an example, a prosthesis may have a tunable forefoot and a tunable heel spring. Additionally, the lateral and medial sides of the forefoot may comprise independently tuned springs. This would allow for adjusting the stiffness set point of the subtalar joint.

Control System

Several control systems can be employed for a variable stiffness prosthesis. One such control system reads sensor information from onboard the prosthesis and worn on the user's body, including inertial measurement units (IMUs), and computes the magnitude of center of mass oscillations and tunes the device stiffness to minimize this magnitude. Prior research has shown that intact biological legs adjust leg stiffness based on the ground compliance and walking/running speed to minimize center of mass oscillations [6]. Another possible control system uses IMUs to measure the walking or running velocity, and to predict the type of terrain, and adjusts the stiffness to the optimal setting. Another control system measures the vertical displacement of the prosthesis or of the contralateral limb during the stance phase, and measures the ground reaction force to calculate the ground compliance, to adjust the prosthesis accordingly. Other control systems use a combination of IMUs, pressure sensors, force sensors, strain gauges, biological sensor data, and motor and joint encoders to calculate prosthesis and environment properties and adjust the stiffness and damping properties accordingly. Device stiffness or damping may be changed under computer control during the swing phase of gait, based upon sensory inputs recorded during stance or of the current or previous gait strides. Alternatively, device state may be adjusted during the stance phase, for example, to adjust the non-linearity of the elastic response. Another control schematic controls the storage and release of strain energy by locking the relative sliding of leaf springs during mid-stance, after the prosthesis has been mechanically moved into a dorsiflexed position by the user, and then releases this energy later in the stride.

Disclosed embodiments allow for changing the stiffness and/or damping of a leaf spring in a quasi-passive way. Applications include but not limited to lower extremity prostheses that can be tuned to the optimal stiffness with a low energy mechanism. Embodiments allow for locking individual leaves in any combination, allowing for a greater number of distinct stiffness settings. In addition, this mechanism allows for preventing leaf springs from sliding relative to each other without inducing high normal forces on the layers. This will lead to much lower rates of surface wear due to friction, which will allow for longer lifespans of products and lower noise. One application is to allow for prosthetic devices to tune stiffness to more closely mimic the behavior of biological limbs, while consuming very little power to allow for lightweight and quiet operation.

FIG. 1 shows the stiffness values of the ankle for various locomotor activities. Average stiffness is shown for slow, medium, and fast walking, descending stairs, and standing. Data is adapted from [5], [7], and [8].

Figure 2:
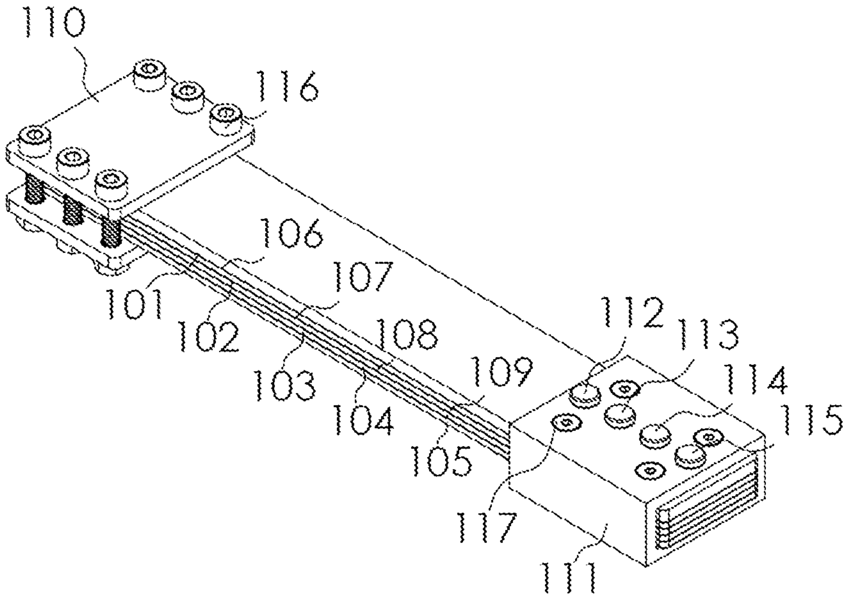
FIG. 2: Pin lock mechanism for tuning spring stiffness, isometric view.

FIG. 2-FIG. 6 show the embodiment of the variable stiffness leaf spring system that uses pins to independently lock and unlock each layer. FIG. 2 shows ground spring 101 mounted to housing 111 via bolts 117. Ground spring 101 can be the same or different thickness as layers 102-105. The mechanical ground in all embodiments can consist of a ground spring such as spring 101 or housing 111 can serve as mechanical ground. In this embodiment and all embodiments described, leaf spring layers 102-105 can be the same or different thicknesses to each other. The leaf spring layers 101-105 can consist of carbon fiber composites, fiber glass, or steel. Bearing surfaces 106-109 are placed between the leaf springs to reduce sliding contact friction and wear. Bearing surfaces 106-109 can consist of Teflon, PTFE, UHWM, or another similar material. Pins 112-115 are inserted into housing 111 to lock or unlock leaves 102-105. Anchor 110 clamps the ends of leaves 101-105 together.

Figure 3:
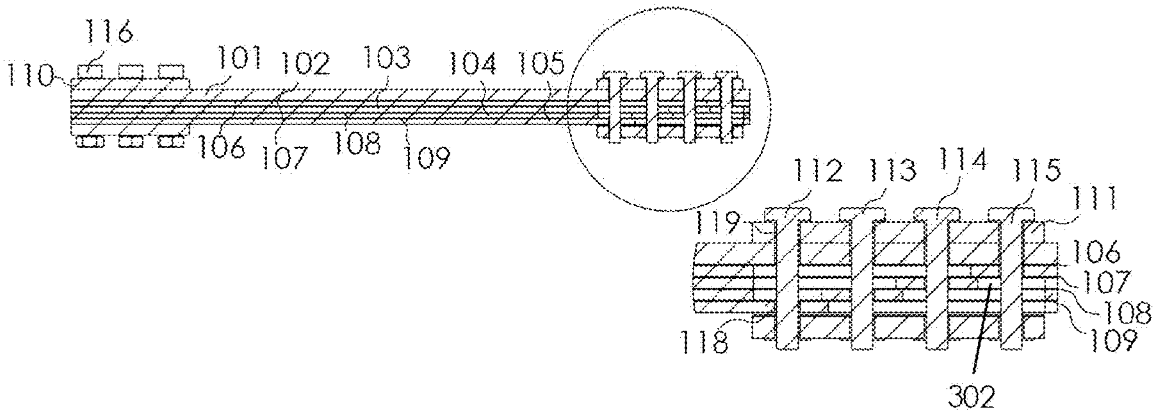
FIG. 3: Section view of pin lock embodiment with zoom in of details.

FIG. 3 shows a cross section of the pin lock embodiment and a detail view of the pin lock mechanism. Leaf spring 101 is the ground spring and is permanently connected to housing 111, leaf 102 is controlled by pin 115, leaf 103 is controlled by pin 114, leaf 104 is controlled by pin 113, and leaf 105 is controlled by pin 112. Metal inserts 118 are mounted into each leaf spring where the pin locks the leaf spring to prevent wear at the pin/leaf spring interface. Bushings 119 are inserted into housing 111 on both sides of the leaf springs. Each leaf spring has slots, e.g., slot 302, for the pins controlling other leaves to slide freely through.

Figure 4:
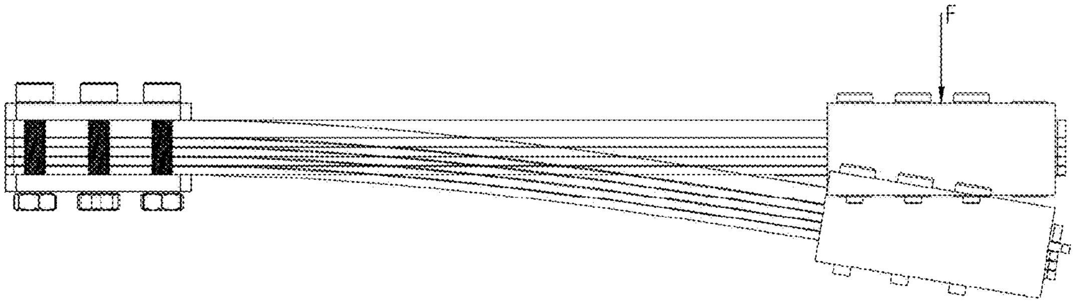
FIG. 4: Deflected state of pin lock mechanism under load, with 1 pin unlocked.
Figure 5:
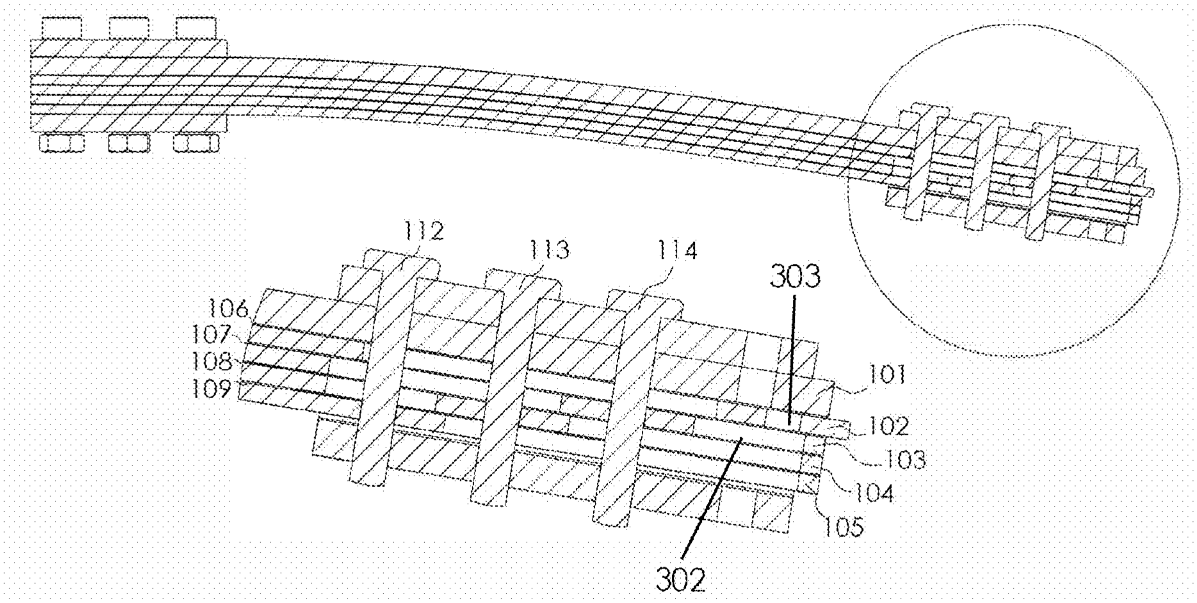
FIG. 5: Section view of pin lock mechanism in deflected state with 1 layer unlocked, with zoomed in view of locking details.

FIG. 4-FIG. 5 show the pin lock embodiment with pin 115 disengaged. When a force is applied to the housing, leaf springs deflect relative to total stiffness. With pin 115 disengaged, leaf 102 is allowed to slide relative to leaves 101, 103, 104, and 105. This decreases the total stiffness of the mechanism compared to having all pins engaged.

Figure 6A:
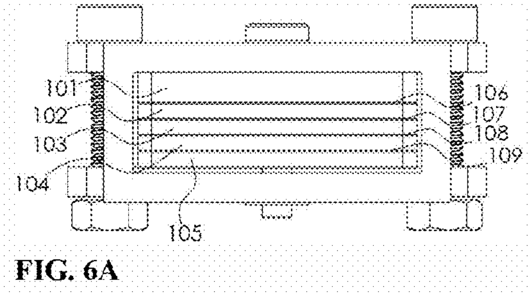
FIGS. 6A and B: End view if pin lock mechanism with FIG. 6A showing flat springs with bearing surface between layers, and FIG. 6B showing springs with linear rail feature between springs to prevent separation.
Figure 6B:
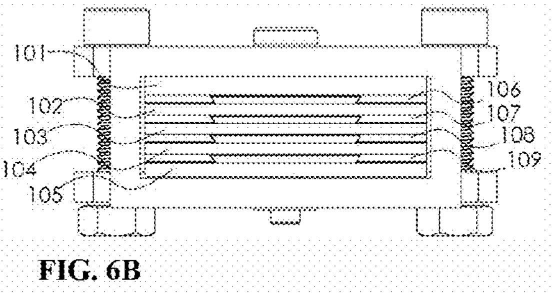

FIGS. 6A and B show different interface options between the leaf springs. FIG. 6A has flat leaf springs 101-105, with bearing surfaces 106-109 between the springs. FIG. 6B has leaf springs with a linear rail feature adhered to one side, such that adjacent leaf springs are prevented from separating by a locking feature. Rails 106-109 are attached between the leaf spring to prevent separation during buckling. These features can be fabricated into the leaf springs directly, or can be made out of a bearing surface such as UHMW, PTFE, or Teflon, and adhered to the leaf springs.

Figure 7:
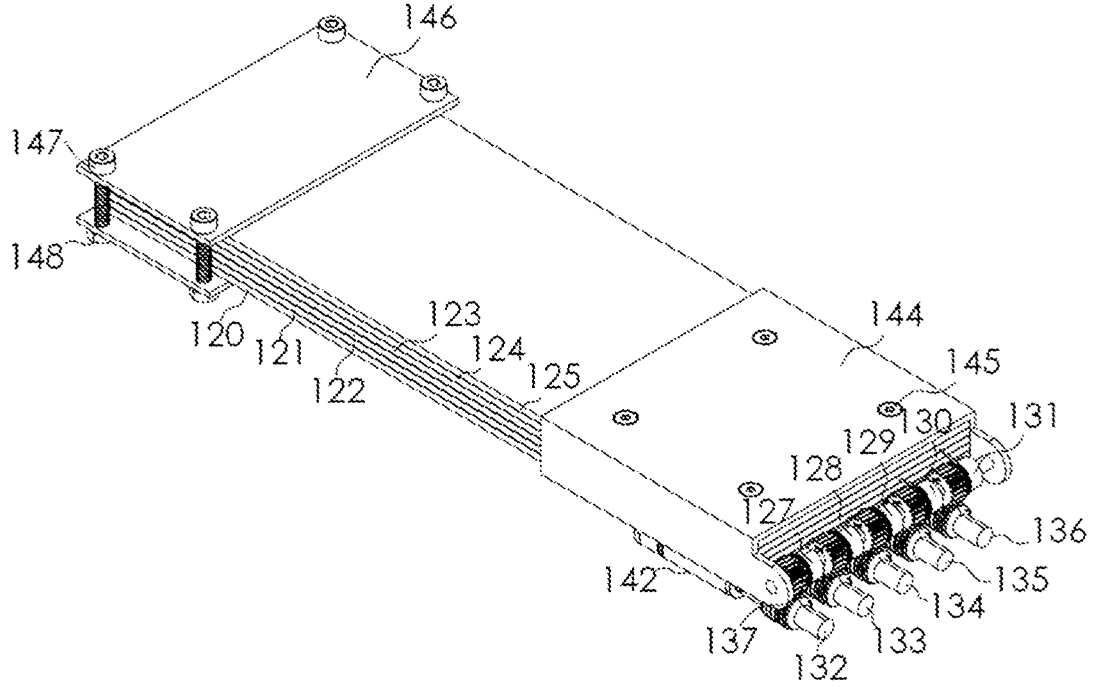
FIG. 7: Isometric view of worm gear embodiment.
Figure 8:
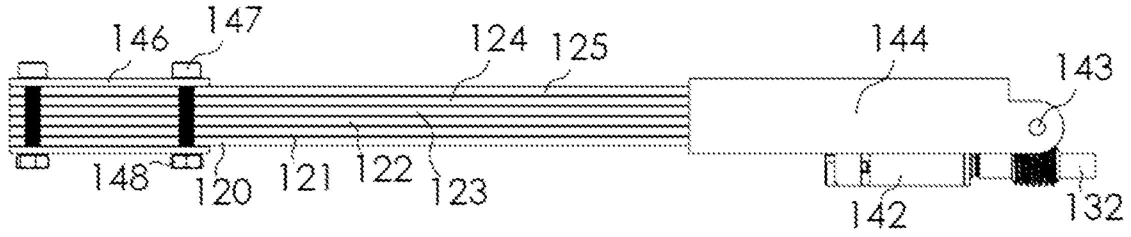
FIG. 8: Side view of worm gear embodiment.

FIG. 7-FIG. 10 show an embodiment of the system that uses a cable driven non-backdrivable worm gear transmission to lock and unlock each leaf spring layer. FIG. 7 shows ground leaf 125 anchored to housing 144 via hex screws 145. Ground link 125 can be the same or different thickness as leaves 120-124. Leaf spring 120-124 are controlled by cables 137-141 on worm gears 127-130. Each leaf has a cable attached to it and the corresponding worm gear adjusts the tension on the cable. Each worm gear is driven by worms 132-136, which are in turn driven by a motor. Depicted in this figure motor 142 drives worm 132 which adjusts the tension of cable 141. Clamp 146 holds each leaf in place and is affixed by bolt 147 and nut 148. The cable driven mechanism locks its respective leaf spring in place when the cable is in tension, increasing bending stiffness of the spring in one direction but not in the direction that causes the cable to be in compression. This embodiment can be used to set a constant bending stiffness, a hardening spring, or a softening spring. To create a hardening spring, cables are kept slack for the first portion of bending and then the worm gears are locked to add tension to the cable, preventing further sliding of independent leaf springs and increasing bending stiffness. To create a softening spring, the work gears are turned off at the beginning of bending to prevent relative sliding between leaf springs, and then the worm gears turn on to add slack to the cable later in bending, decreasing the stiffness.

Figure 9:
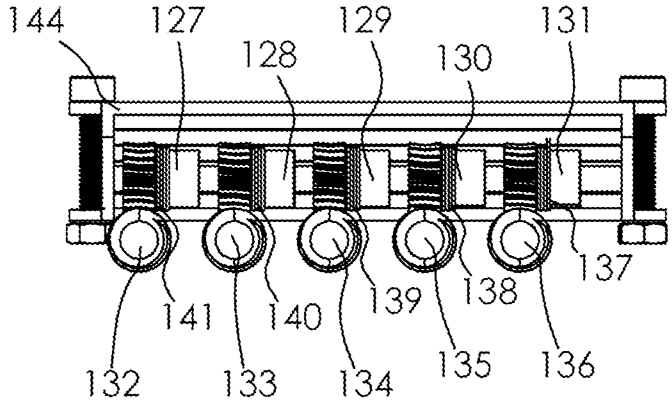
FIG. 9: Front view of worm gear embodiment.

FIG. 9 shows an end view of the worm gear mechanism, showing worms 132-136 driving worm gears 127-131 to control the tension of cables 137-141.

Figure 10:
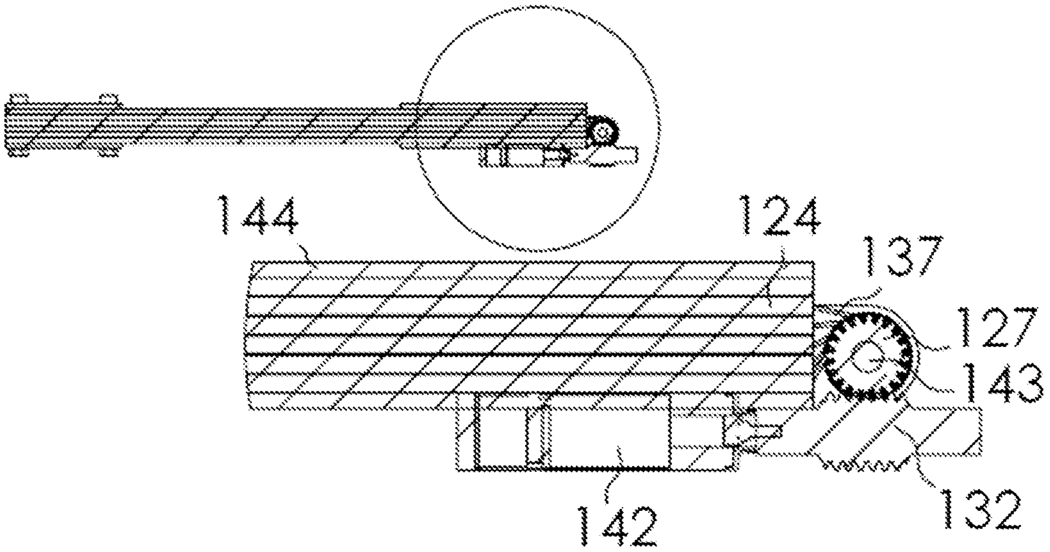
FIG. 10: Detail view of worm gear mechanism.

FIG. 10 shows a cross section view of the worm gear embodiment. Leaf spring 124 is attached to cable 137, which wraps around worm gear 127 to control tension of the cable. Worm 132 is driven by motor 142 to adjust the position of worm gear 127 to adjust the tension on cable 137. Worm gear 127 rotates on shaft 143 which is mounted to housing 144.

Figure 11:
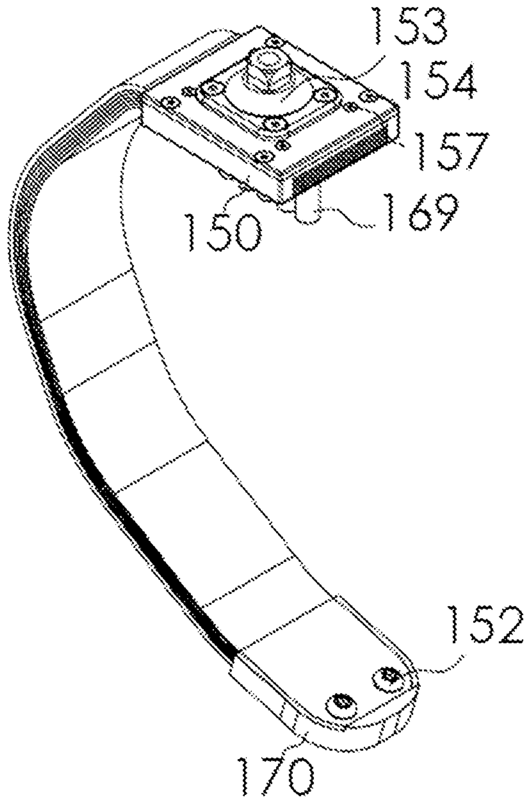
FIG. 11: Isometric view of solenoid mechanism in lower extremity prosthesis.
Figure 12:
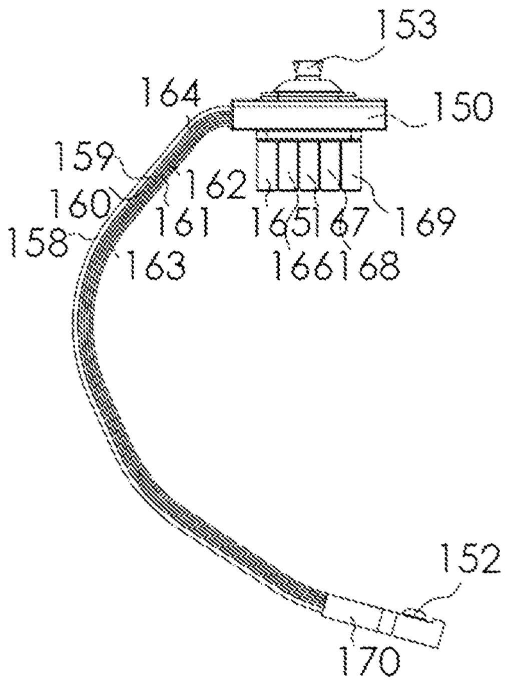
FIG. 12: Side view of prosthesis mechanism.
Figure 13:
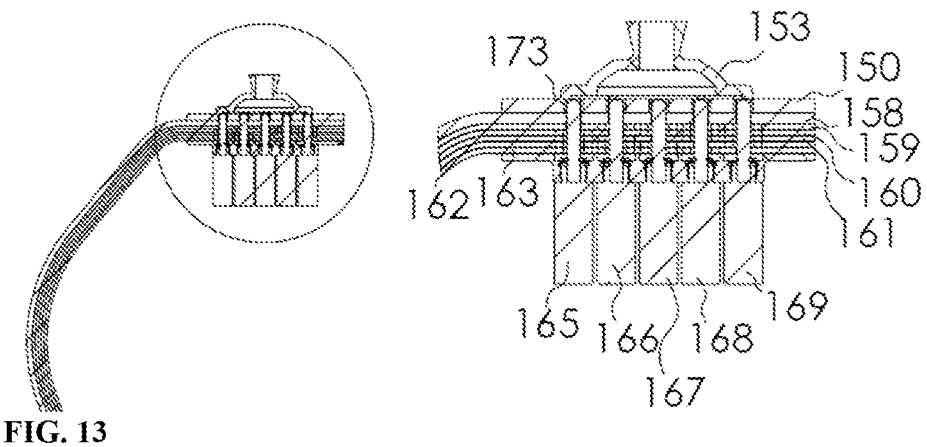
FIG. 13: Detail view of solenoid prosthesis embodiment.

FIG. 11-FIG. 17 show another embodiment of the pin locking mechanism. In this embodiment the leaf springs are configures as a lower extremity prosthesis. Each pin, e.g., pin 173 (FIG. 13), is controlled by a solenoid mechanism. FIG. 11 shows an isometric view of the variable stiffness prosthesis. FIG. 12 shows a side view of the prosthesis. Ground spring 158 is permanently attached to housing 150 via fasteners 157. Leaf springs 158-163 are controlled by solenoids 165-169. Pyramid adapter 153 is mounted on housing 150 to allow the prosthesis to be attached to a standard prosthetic socket. FIG. 13 shows a cross section view of the solenoid mechanism. Solenoid 165 locks and unlocks leaf spring 159, solenoid 166 controls leaf spring 160, solenoid 167 controls leaf 161, solenoid 168 controls leaf spring 162, and solenoid 169 controls leaf 163. A hole in each leaf spring engages with a solenoid to lock it to a mechanical ground, while a slot in the other leaf springs allow the springs not corresponding to that solenoid to slide freely, similar to the slots, e.g., slot 302, and holes, e.g., hole 303, shown in FIG. 5.

Figure 14:
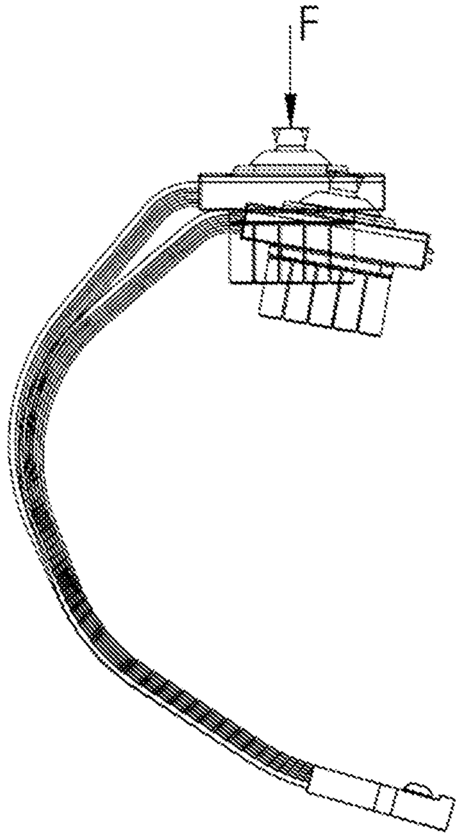
FIG. 14: Prosthesis embodiment in deflected state.
Figure 15:
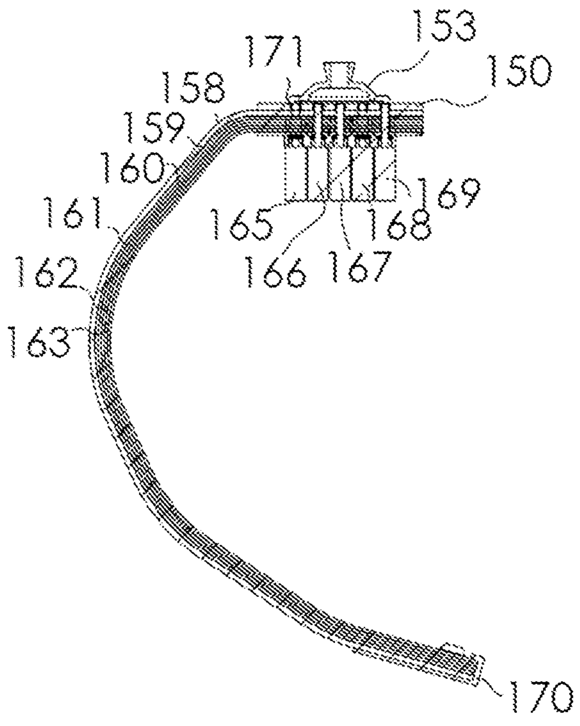
FIG. 15: Section view of prosthesis embodiment with several solenoids unlocked.
Figure 16:
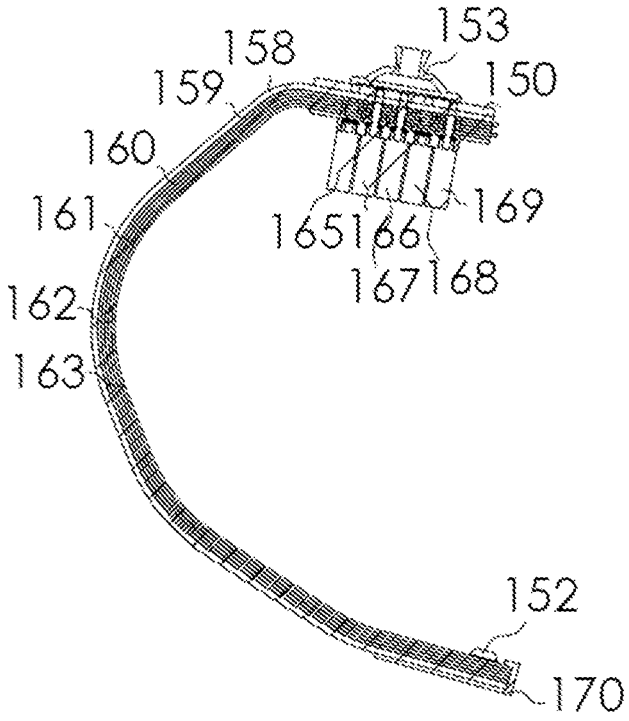
FIG. 16: Section view of prosthesis embodiment in deflected state.
Figure 17:
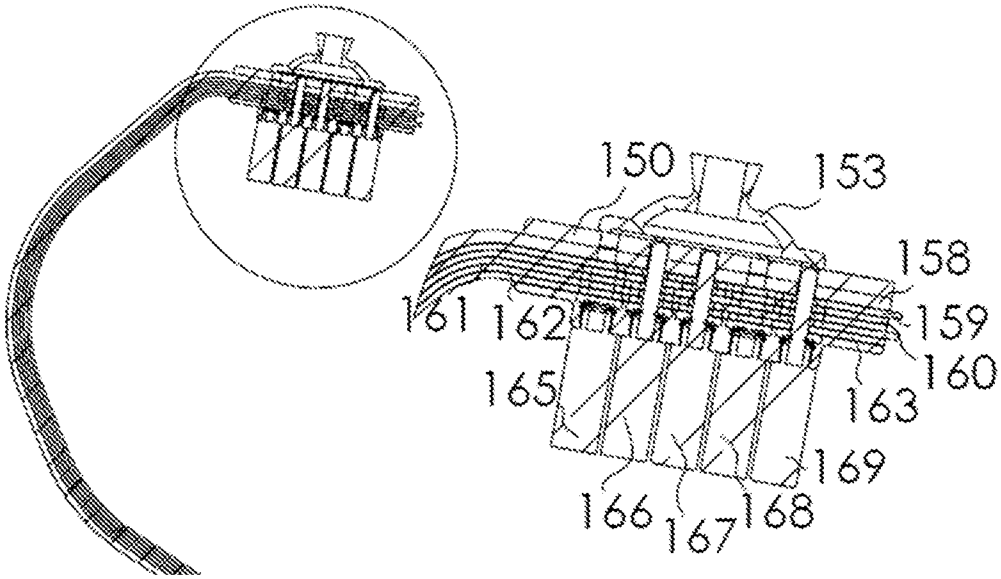
FIG. 17: Detail view of prosthesis embodiment while deflected under load.

FIG. 14-FIG. 17 shows this embodiment when 2 of the pins are disengaged. FIG. 14 shows the deflection of the prosthesis that occurs when a force is applied to the pyramid adapter. FIG. 15-FIG. 17 shows that solenoids 165 and 168 have the pins disengaged from leaf springs 159 and 162. When a load is applied to pyramid adapter 153 as in FIG. 16, leaf springs 159 and 162 are allowed to slide relative to housing 150, and springs 158, 160, 161, and 163, decreasing the overall stiffness of the system. FIG. 17 shows a detailed view of the solenoid locking mechanism with two leaves unlocked as in FIG. 16. Solenoids 165-169 can be lock and unlocked in any combination, allowing for the number of stiffness settings of a device with n layers to be equal to C(n, 1)+C(n, 2)+ . . . +C(n, n).

Figure 18:
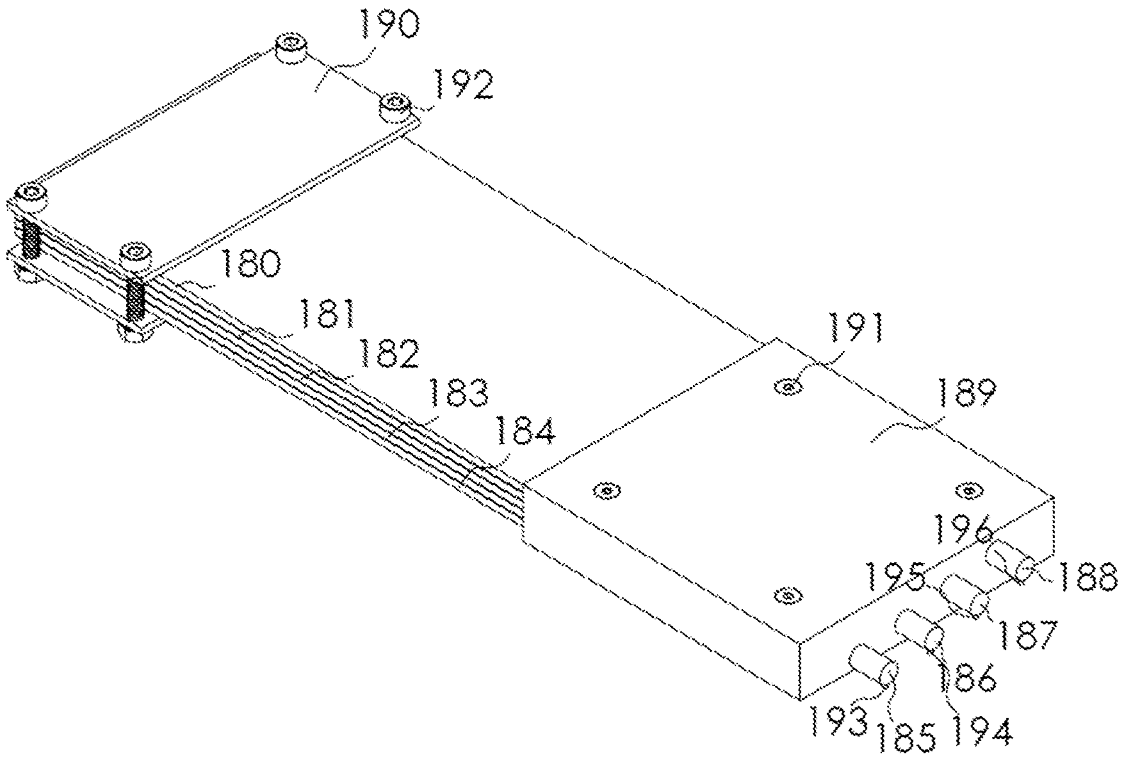
FIG. 18: Isometric view of variable dampening hydraulic piston system.
Figure 19:
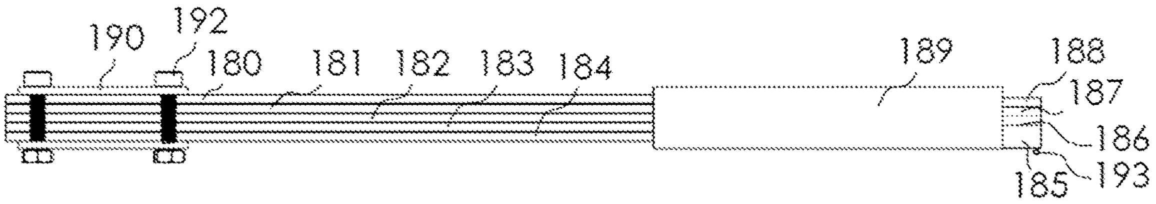
FIG. 19: Side view of variable dampening hydraulic piston embodiment.
Figure 20:
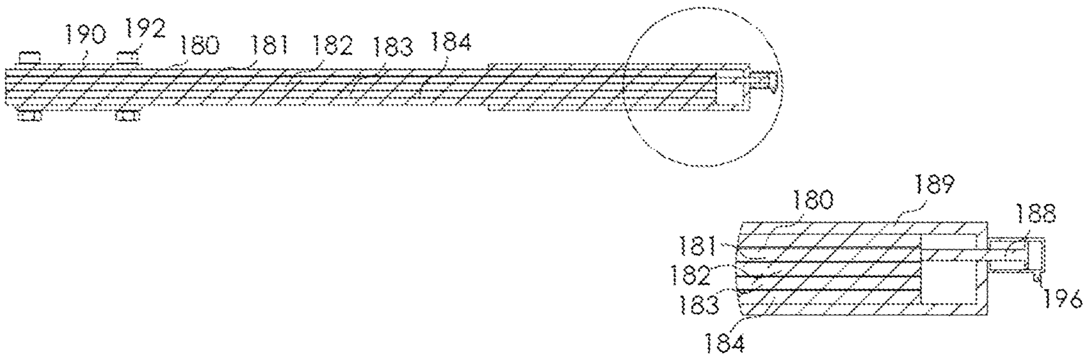
FIG. 20: Detailed section view of variable dampening embodiment.

FIG. 18-FIG. 20 show an embodiment of the invention that uses a hydraulic damper attached to each layer in order to tune the damping properties in addition to stiffness. FIG. 18 shows an isometric view of this embodiment, ground leaf 180 is permanently attached to housing 189 via screws 191. Leaf springs 181-184 are connected to dampers 185-188. Each damper can be controlled by opening valves 193-196 to allow the leaf spring to move freely, or selectively tuning the damping effects by closing the valve. This embodiment can dissipate energy to control the mechanical properties of the mechanism. This embodiment can be used in conjunction with the stiffness control embodiments or independently. The valves on the dampers can be tuned to control the behavior of the springs as a function of the velocity of bending.

FIG. 19 shows a side view of the variable dampening hydraulic embodiment.

FIG. 20 shows a section view and detailed view of the hydraulic piston. Hydraulic damper 188 is controlled by opening or closing valve 196. This tunes the dampening properties of leaf spring 181.

Figure 21:
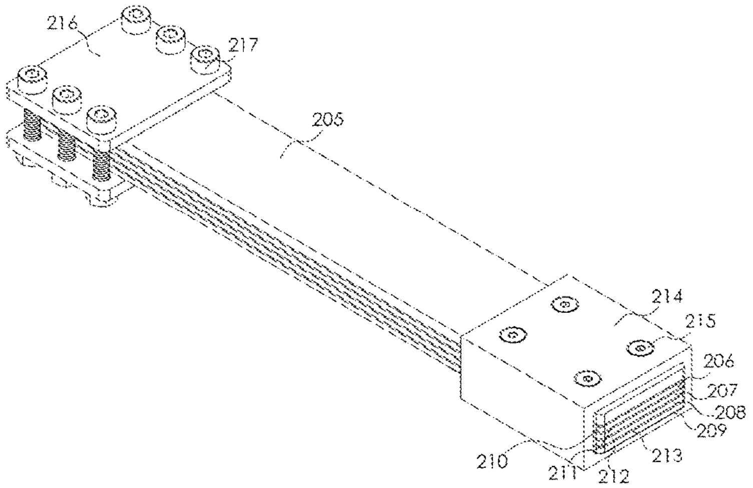
FIG. 21: Isometric view of electrostatic clutch configuration.
Figure 22:
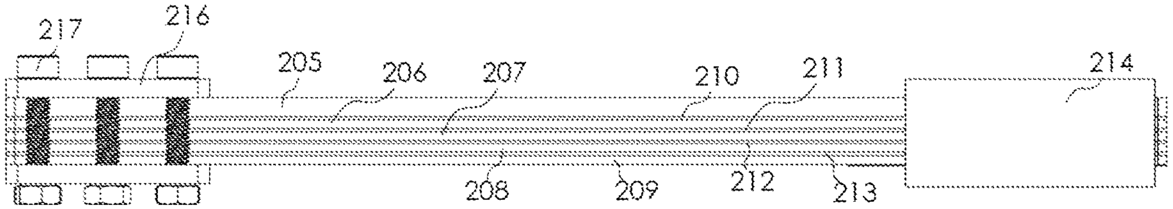
FIG. 22: Side view of electrostatic clutch configuration.

FIG. 21 and FIG. 22 show an embodiment using electrostatic clutches between layers. Leaf spring 205 is permanent attached to housing 214 with screws 215. Leaf springs 206-209 can be locked and unlocked by electrostatic layers 210-213. Electrostatic clutch 210 prevents relative motion between leaf spring 206 and ground spring 205, clutch 211 prevents motion between spring 206 and 207, clutch 212 prevents relative motion between spring 207 and 208, and clutch 213 prevents relative motion between springs 208 and 209.

Figure 23:
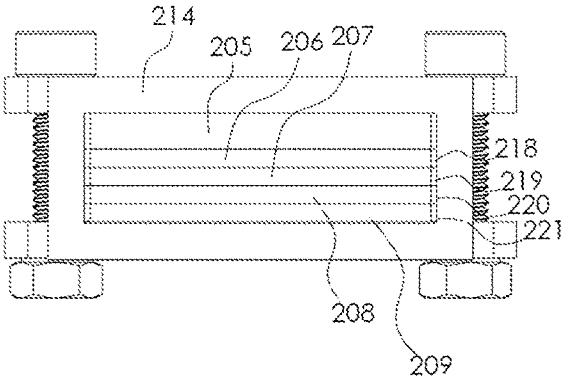
FIG. 23: End view of electrostatic clutch device where leaf springs are mechanically locked to the mechanical ground through the use of an electrostatic clutch.

FIG. 23 shows an electrostatic clutch configuration in which electrostatic clutches 218-221 are between springs 206-209 and housing 214 in order to allow for independent locking of each leaf spring to the mechanical ground.

Figure 24:
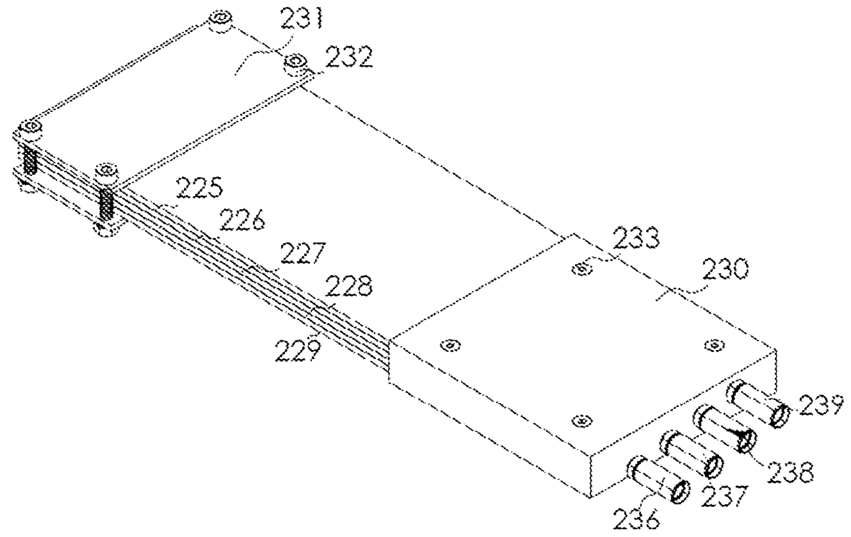
FIG. 24: Isometric view of non-backdrivable lead screw embodiment.
Figure 25:
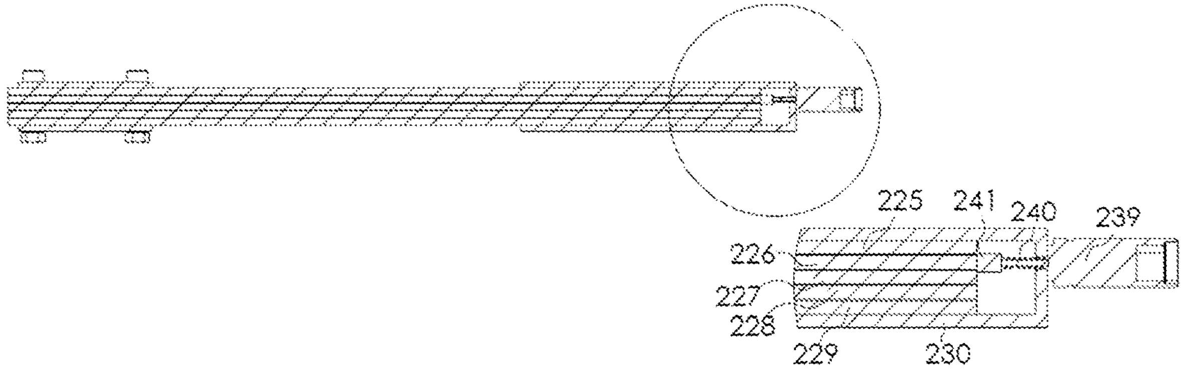
FIG. 25: Detailed section view of linear actuator system.

FIG. 24-FIG. 25 show a non-backdrivable lead screw embodiment. Ground spring 225 is permanently attached to housing 230 with screws 233. Leaf springs 226-229 can be locked and unlocked with actuators 236-239. Clamp 231 attaches the other end of the springs together, held by screws 232. Similar to the worm gear cable driven embodiment in FIG. 7-FIG. 10, This embodiment can be used to set a constant bending stiffness, a hardening spring, or a softening spring. To create a hardening spring, linear actuators move out of the way of the leaf springs for the first portion of bending, and then the linear actuator is turned off, causing the non-backdrivable transmission preventing further sliding of independent leaf springs, and therefore increasing bending stiffness. To create a softening spring, the linear actuators are locked to prevent sliding of leaf springs during the beginning if bending, and then the linear actuators are turned on to move out of the way of the leaf springs and allow them to slide relative to each other, decreasing the stiffness.

FIG. 25 shows a detailed view of the linear actuator embodiment. Leaf springs 226-229 are each controlled by an independent non-backdrivable linear actuator. Lead screw 240 is driven by motor 239 to extend or contract, by driving nut 241 which is connected to leaf spring 226. This adjusts where the leaf spring end will be held when the actuator is turned off.

Figure 26:
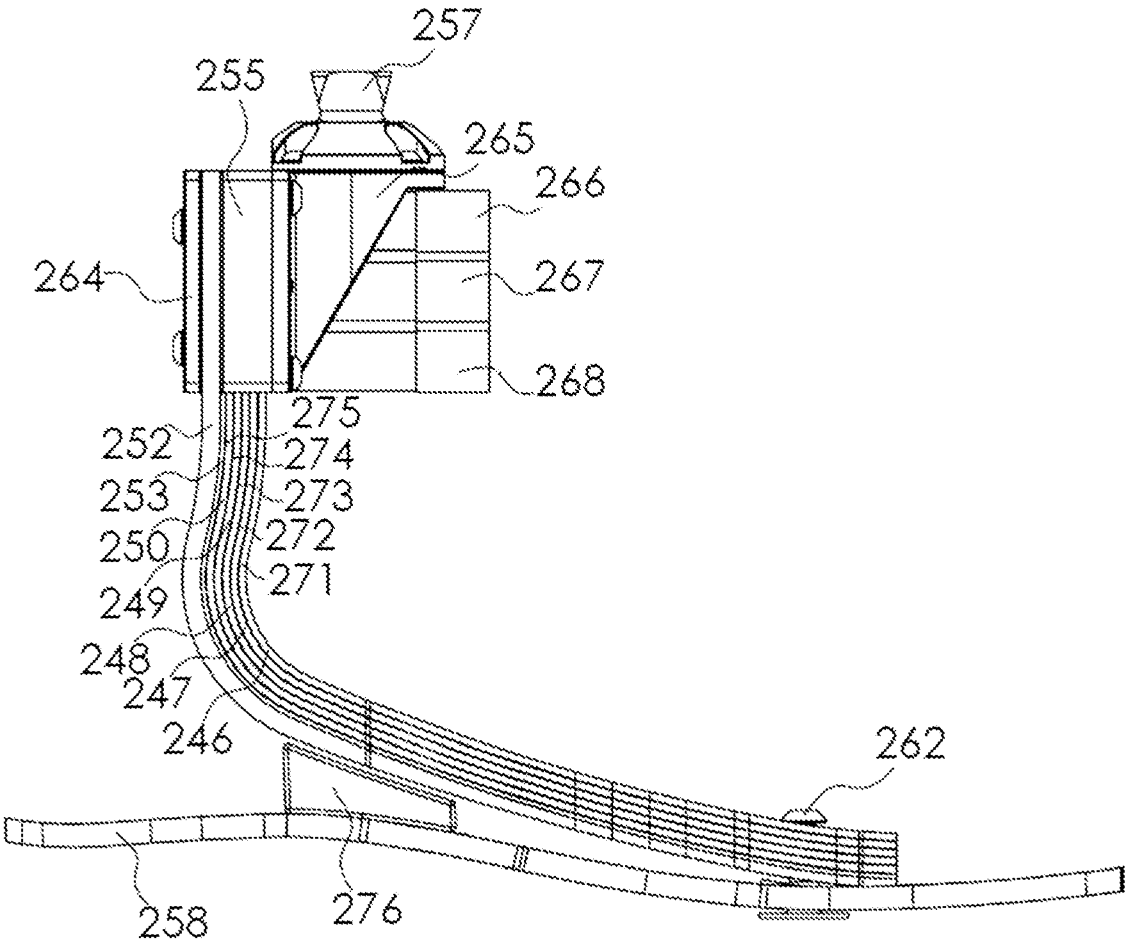
FIG. 26: Prosthesis embodiment with tuneable leaf springs and fixed stiffness heel spring.
Figure 27:
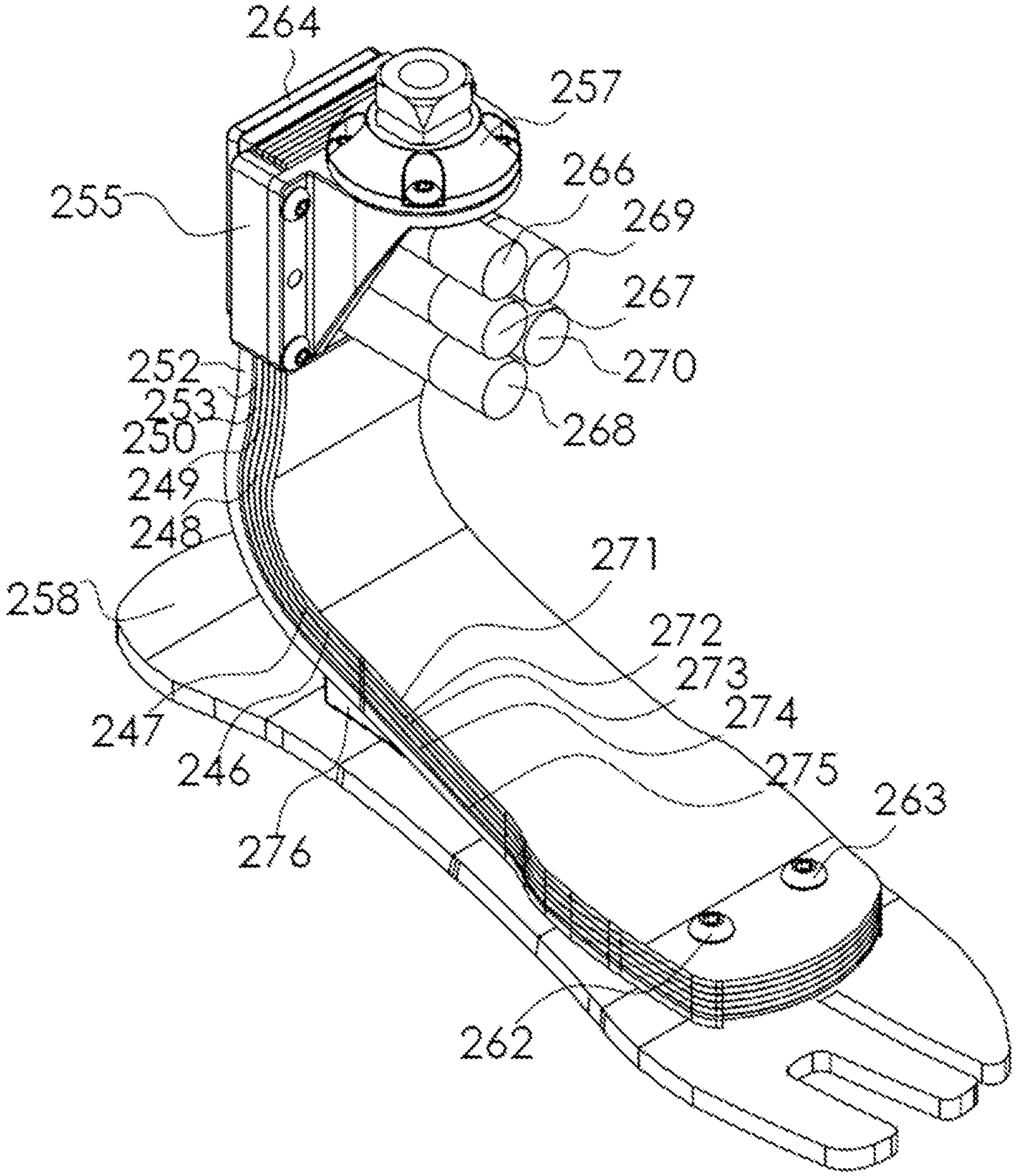
FIG. 27: Isometric view of prosthesis embodiment with leaf springs controlled by solenoid actuators.

FIG. 26-FIG. 27 show the invention configured as a foot prosthesis. FIG. 26 shows ground spring 252 clamped between housing 255 and clamp 264 with bolts 261 as well as an adhesive joint. Tuneable springs 246-250 can be locked to housing 255 with solenoids 266-270, or unlocked to slide freely. Spacer 254 allows for space for the clamping mechanism for ground spring 252. Spacer 254 can be made of additional carbon fiber, or a less stiff material such as PTFE, P-Tex, Teflon, etc. Pyramid adapter 257 allows for the prosthesis to be attached to a prosthetic socket. Actuator housing 265 is fastened to housing 255. Heel spring 258 is attached to ground spring 252 though bolts 260 as well as adhesive. In this configuration heel spring 258 is a fixed stiffness, but heel spring 258 can also be composed of multiple lockable layers in order to independently control the stiffness of the heel spring.

FIG. 27 shows an isometric view of the prosthesis configuration. Solenoids 266-270 independently control the locking of leaf spring 246-250. The interface between the solenoids and the leaf springs consists of holes to lock the leaf spring to be controlled, and slots for the other leaf springs to be able to slide, as shown in FIG. 5. Leaf springs 246-250 and ground spring 252 are clamped together at the toe with bolts 262 and 263.

Figure 28:
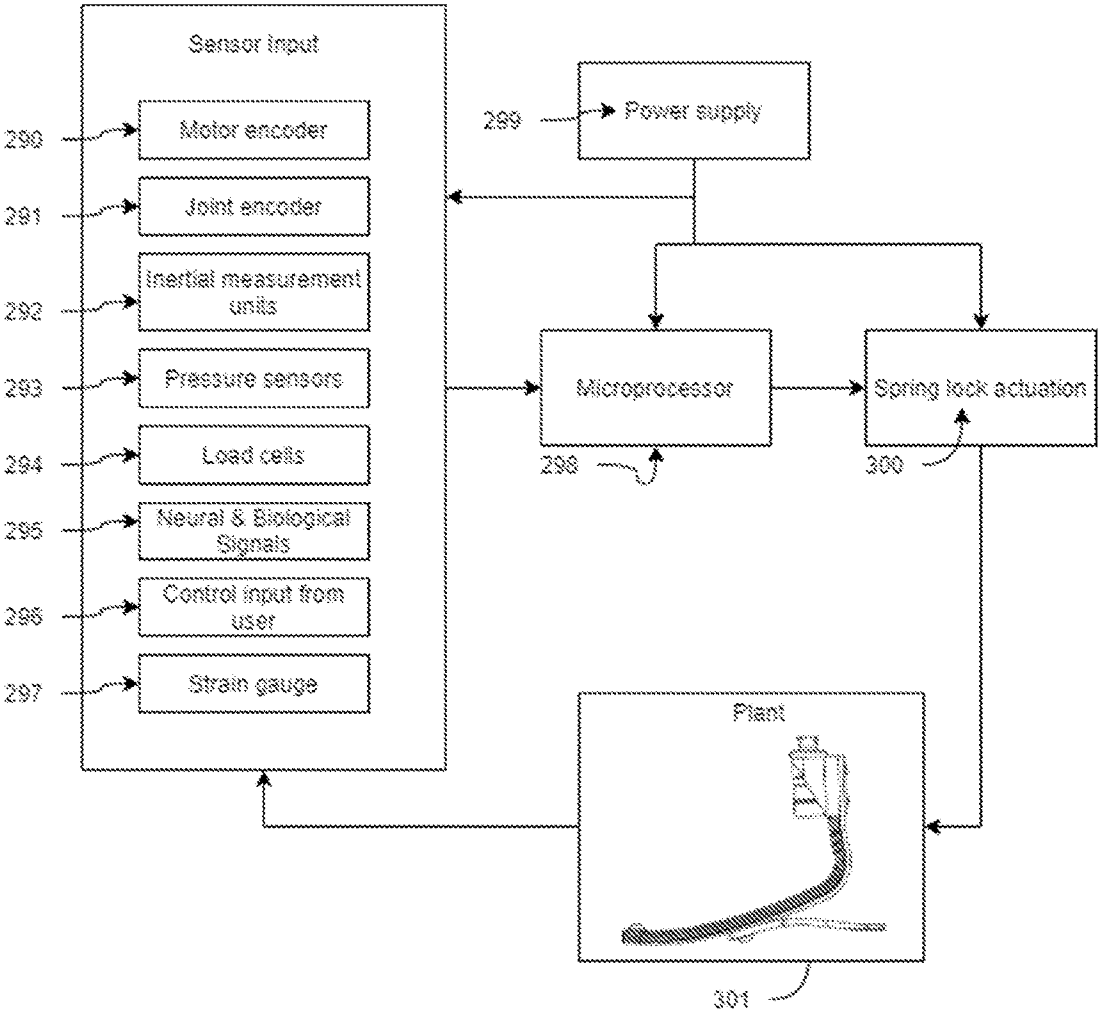
FIG. 28: Block diagram of overall control architecture.

FIG. 28 shows a block diagram of the system. Sensor inputs 290-297 from onboard the device measures joint angle, actuator state, acceleration, orientation, force, pressure, and additional inputs. Sensors can also be worn on the users' body and contralateral limb. Neural and biological signals 295 may include electromyographic sensors, muscle length and speed sensors, nerve cuffs, and metabolic measurements. Sensors 290-297 are used to determine the optimal device stiffness by an algorithm running on the onboard microprocessor 298. Microprocessor 298 controls spring lock actuation system 300 to reach the desired stiffness state. Spring lock actuation 290 controls the stiffness or dampening properties of the physical plant 301, which in this case is the prosthesis. The onboard sensors 290-297, microprocessor 298, and actuation system 300 are powered by portable power supply 299.

Figure 29:
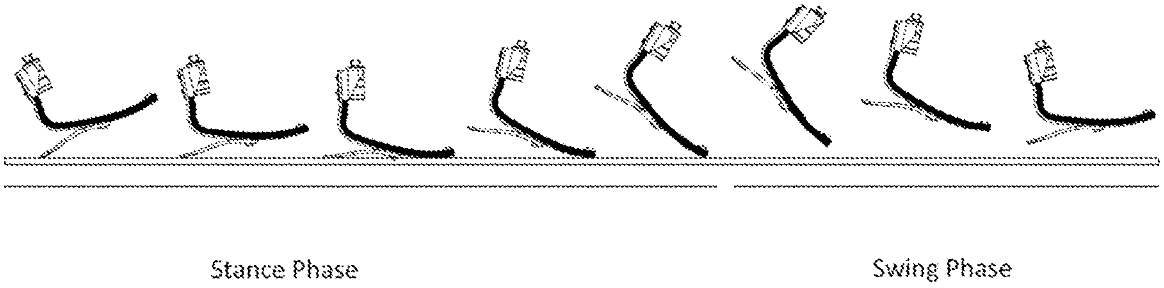
FIG. 29: Gait cycle of walking, showing prosthesis in stance phase and swing phase.

FIG. 29 shows the prosthesis during a typical walking gait cycle. Control inputs for the device can be measured from the sensors onboard the device and on the user's body during stance phase or swing phase. During one possible control schematic, ground compliance is measured during the stance phase of walking, by calculating the relative vertical displacement of the ground using onboard IMU sensors. This displacement along with force measurements is used to calculate ground stiffness, and prosthesis stiffness is adjusted accordingly. This would allow for the prosthesis to become stiffer while locomoting on more compliant ground, and for the prosthesis to become less stiff while ambulating across stiffer terrain, as is seen in biological limbs. Another possible control scheme calculates the walking speed and terrain using onboard sensors, adjusting the stiffness accordingly to achieve biomimetic functionality. The stiffness states can be adjusted during the swing phase of walking based upon data gathered within the current stride, or data gathered from previous strides. Additionally, as the prosthesis is loaded during mid-stance and bends into a dorsi-flexed position, the springs can be locked in order to store strain energy, and unlocked later in the stride to release the stored energy.

Figure 30:
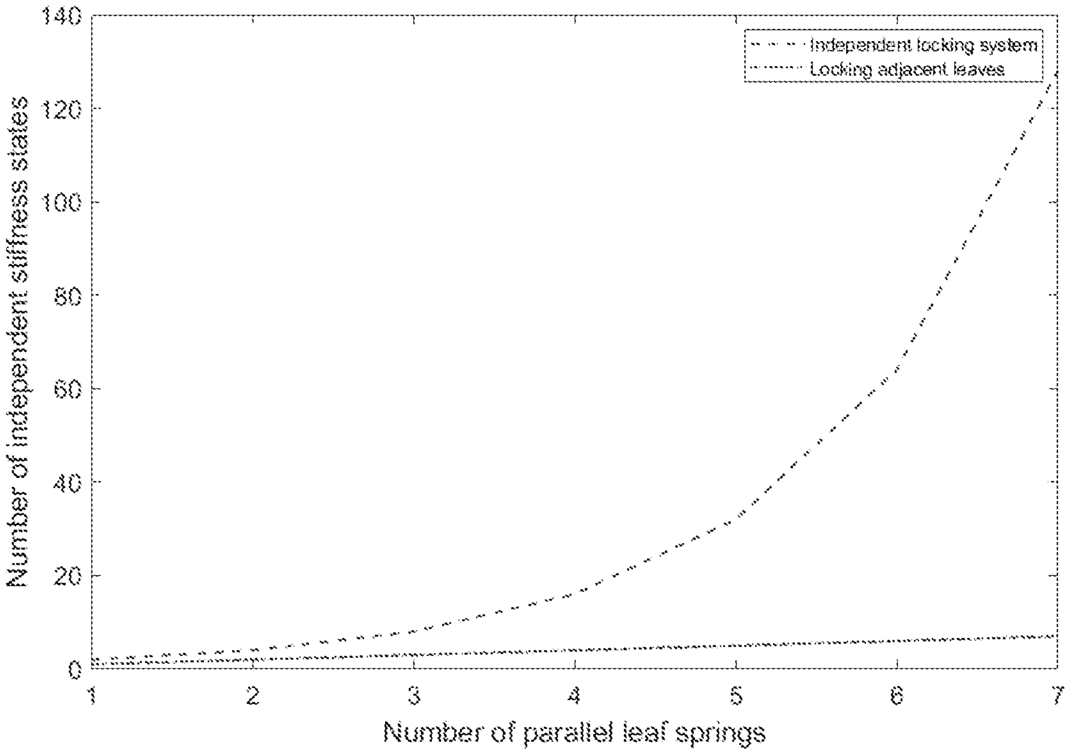
FIG. 30: Compares the number of independent locking states between prior art and the proposed invention.

FIG. 30 shows the number of independent stiffness states for the proposed invention which locks layers independently from each other compared to the prior art, which only allows for locking adjacent springs in ascending order. This increase in stiffness states allows for finer resolution of stiffness control.

Figure 31:
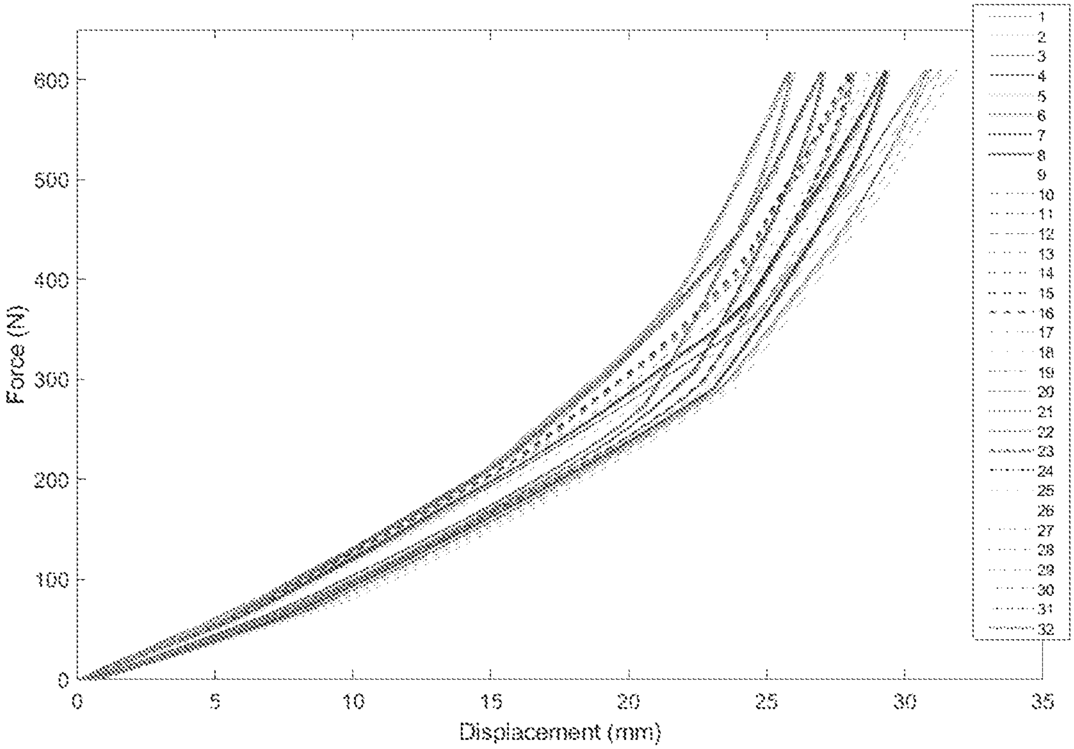
FIG. 31: Measured prototype force-deflection curves during benchtop testing on an Intron Materials Testing System.

FIG. 31 shows the force-deflection curves of the variable stiffness prosthesis prototype as measured during benchtop testing for each independent stiffness state for a prosthesis with five independently controlled leaf springs. The slope of each plotted line demonstrates the stiffness of the device for that state. State 1 corresponds to the lowest stiffness state in which all springs are unlocked, and State 32 corresponds to the highest stiffness state in which all 5 springs are locked.

The relevant teachings of all patents, published applications and references cited herein are incorporated by reference in their entirety.

REFERENCES

[1] H. Herr, "Variable-Mechanical-Impedence Artificial Legs". U.S. Pat. No. 64,195, 2004.

[2] R. J. Christensen, "Prosthetic foot with energy transfer medium including variable viscosity fluid". United States of America Patent U.S. Pat. No. 6,663,673B2, 16 Dec. 2003.

[3] E. M. Glanzer and P. G. Adamczyk, "Design and Validation of a Semi-Active Variable Stiffness Foot Prosthesis," *IEEE Trans Neural Syst Rehabil Eng.,* 2018.

[4] E. J. Rouse and M. K. Shepherd, "Biomimetic and variable stiffness ankle system and related methods". United States of America U.S. Pat. No. 92,761, 5 Apr. 2018.

[5] M. K. Shepherd and E. J. Rouse, "The VSPA Foot: A Quasi-Passive Ankle-Foot Prosthesis With Continuously Variable Stiffness," *IEEE Trans Neural Syst Rehabil Eng,* 2017.

[6] D. Ferris, M. Louie and C. Farley, "Running in the real world: adjusting leg stiffness for different surfaces," Proceedings of the Royal Society B, vol. 265, pp. 989-994, 1998.

[7] G. Bovi, M. Rabuffetti, P. Mazzoleni and M. Ferrarin, "A multiple-task gait analysis approach: kinematic, kinetic and EMG reference data for healthy young and adult subjects," *Gait & Posture*, vol. 33, no. 1, 2011.

[8] I. D. Loram and M. Lackie, "Direct measurement of human ankle stiffness during quiet standing: the intrinsic mechanical stiffness is insufficient for stability," *The Journal of Physiology,* 2002.

What is claimed is:

1. A variable stiffness spring assembly comprising:

multiple leaf springs joined to bend together and to slide relative to each other, with ends of the leaf springs displaced axially relative to each other with bending;

a mechanical ground;

multiple actuators, each actuator associated with an individual leaf spring of the multiple leaf springs, each actuator limiting axial displacement of an end of the associated individual leaf spring relative to the mechanical ground independent of other leaf springs; and a controller configured to control each actuator.

2. The variable stiffness spring assembly as claimed in claim 1 wherein each actuator limits axial displacement of the individual end of the spring by locking the end of the individual spring to the mechanical ground.

3. The variable stiffness spring assembly as claimed in claim 2 wherein each actuator locks the end of the individual spring to the mechanical ground by extending a pin through the individual spring and the mechanical ground.

4. The variable stiffness spring assembly as claimed in claim 3 wherein the pin extends through slots in leaf springs other than the individual spring.

5. The variable stiffness spring assembly as claimed in claim 2 wherein each actuator locks the end of the individual spring to the mechanical ground through an electrostatic clutch.

6. The variable stiffness spring assembly as claimed in claim 1 wherein each actuator limits axial displacement of an end of the individual spring by applying tension to a cable coupled between the end of the individual spring and the mechanical ground.

7. The variable stiffness spring assembly as claimed in claim 6 wherein the cable is controlled through a worm gear.

8. The variable stiffness spring assembly as claimed in claim 1 wherein each actuator limits axial displacement of the end of the individual spring through a variable damper coupled between the end of the individual spring and the mechanical ground.

9. The variable stiffness spring assembly as claimed in claim 1 wherein each actuator limits axial displacement of the end of the individual spring through a lead screw coupled between the end of a leaf spring and the mechanical ground.

10. The variable stiffness spring assembly as claimed in claim 9 wherein the actuator is a motor that rotates the lead screw.

11. The variable stiffness of spring assembly as claimed in claim 9 wherein the actuator is a variable damper coupled to the lead screw.

12. The variable stiffness spring assembly as claimed in claim 9 wherein the actuator is a clutch coupled to the lead screw.

13. The variable stiffness spring assembly as claimed in claim 1 wherein the mechanical ground comprises a ground spring.

14. A variable stiffness spring assembly as claimed in claim 1 configured as a lower extremity prosthesis.

15. A method of varying spring stiffness comprising:

providing multiple leaf springs joined to bend together and to slide relative to each other, with ends of the leaf springs displaced axially relative to each other with bending, and a mechanical ground; and limiting axial displacement of an end of each leaf spring relative to the mechanical ground independent of other leaf springs.

16. The method as claimed in claim 15 wherein axial displacement is limited by multiple actuators, each actuator associated with an individual leaf spring of the multiple leaf springs, and a controller configured to control each actuator.

17. The method as claimed in claim 16 wherein each actuator limits axial displacement of the associated individual end of the spring by locking the end of the associated individual spring to the mechanical ground.

18. The method as claimed in claim 17 wherein each actuator locks the end of the individual spring to the mechanical ground by extending a pin through the individual spring and the mechanical ground.

19. A method as claimed in claim 15 applied to a lower extremity prosthesis.

* * * * *